US008025621B2

(12) United States Patent
Ewaschuk et al.

(10) Patent No.: US 8,025,621 B2
(45) Date of Patent: Sep. 27, 2011

(54) MEDICAL DEVICE WITH ADJUSTABLE INNER SHAFT MOVEMENT

(75) Inventors: Michael Ewaschuk, Haverhill, MA (US); Peter Aliski, Malden, MA (US)

(73) Assignee: Microline Surgical, Inc., Beverly, MA (US)

( * ) Notice: Subject to any disclaimer, the term of this patent is extended or adjusted under 35 U.S.C. 154(b) by 1410 days.

(21) Appl. No.: 11/188,704

(22) Filed: Jul. 26, 2005

(65) Prior Publication Data

US 2007/0078483 A1    Apr. 5, 2007

(51) Int. Cl.
*A61B 17/00* (2006.01)
*A61B 1/32* (2006.01)

(52) U.S. Cl. ........................ 600/204; 606/205

(58) Field of Classification Search .......... 600/200–206; 251/366; 606/204–205; 604/158
See application file for complete search history.

(56) References Cited

U.S. PATENT DOCUMENTS

| 5,178,133 | A | * | 1/1993 | Pena | 600/203 |
|---|---|---|---|---|---|
| 5,235,966 | A | * | 8/1993 | Jamner | 600/204 |
| 5,308,358 | A | * | 5/1994 | Bond et al. | 606/205 |
| 5,318,570 | A | * | 6/1994 | Hood et al. | 606/99 |
| 5,370,659 | A | * | 12/1994 | Sakashita | 606/205 |
| 5,496,331 | A | * | 3/1996 | Xu et al. | 606/139 |
| 5,514,157 | A | * | 5/1996 | Nicholas et al. | 606/206 |
| 5,755,726 | A | * | 5/1998 | Pratt et al. | 606/143 |
| 5,785,647 | A | * | 7/1998 | Tompkins et al. | 600/201 |
| 5,810,863 | A | * | 9/1998 | Wolf et al. | 606/185 |
| 5,810,879 | A | * | 9/1998 | de Guillebon | 606/205 |
| 5,817,119 | A | * | 10/1998 | Klieman et al. | 606/174 |
| 5,827,279 | A | * | 10/1998 | Hughett et al. | 606/45 |
| 5,899,913 | A | * | 5/1999 | Fogarty et al. | 606/159 |
| 6,015,426 | A | * | 1/2000 | Griffiths | 606/205 |
| 6,074,408 | A | * | 6/2000 | Freeman | 606/205 |
| 6,090,129 | A | * | 7/2000 | Ouchi | 606/206 |
| 6,248,092 | B1 | * | 6/2001 | Miraki et al. | 604/96.01 |
| 6,264,604 | B1 | * | 7/2001 | Kieturakis et al. | 600/207 |

(Continued)

FOREIGN PATENT DOCUMENTS

JP    6-7366    1/1994

(Continued)

OTHER PUBLICATIONS

U.S. Appl. No. 11/179,509 to Ewaschuk, filed Jul. 13, 2005.

(Continued)

*Primary Examiner* — Thomas C. Barrett
*Assistant Examiner* — Matthew Lawson
(74) *Attorney, Agent, or Firm* — Greenblum & Bernstein, P.L.C.

(57) ABSTRACT

A medical device may include a tube having a first end and a second end, in which the first end can engage an instrument tip, an inner shaft disposed in the tube, a shaft end connected to the inner shaft and which can move lengthwise relative to the tube, a first abutment surface to abut a first shaft end stop of the shaft end, and a second abutment surface to abut a second shaft end stop of the shaft end generally opposite the first shaft end stop of the shaft end, in which the shaft end can slidably move along a length constrained by the abutment of the first shaft end stop against the first abutment surface and the second shaft end stop against the second abutment surface, and in which either one or both of the first abutment surface or the second abutment surface is positionally adjustable relative to the tube.

20 Claims, 4 Drawing Sheets

U.S. PATENT DOCUMENTS

| | | | |
|---|---|---|---|
| 6,383,134 B1 * | 5/2002 | Santilli | 600/205 |
| 6,428,092 B1 * | 8/2002 | Friedmann et al. | 296/223 |
| 6,443,909 B1 * | 9/2002 | Ouchi | 600/562 |
| 6,447,511 B1 * | 9/2002 | Slater | 606/48 |
| 6,451,042 B1 * | 9/2002 | Bonutti | 606/190 |
| 6,592,602 B1 * | 7/2003 | Peartree et al. | 606/170 |
| 6,613,068 B2 * | 9/2003 | Ouchi | 606/205 |
| 7,097,648 B1 * | 8/2006 | Globerman et al. | 606/99 |
| 7,122,028 B2 * | 10/2006 | Looper et al. | 606/1 |
| 2001/0056279 A1 * | 12/2001 | Odell et al. | 606/41 |
| 2002/0095177 A1 * | 7/2002 | Kupferschmid et al. | 606/205 |
| 2004/0034381 A1 * | 2/2004 | Shedlov | 606/180 |
| 2004/0143163 A1 * | 7/2004 | Palmer et al. | 600/204 |
| 2004/0172057 A1 | 9/2004 | Guillebon et al. | |
| 2004/0254425 A1 * | 12/2004 | Vierra et al. | 600/204 |
| 2006/0195084 A1 * | 8/2006 | Slater | 606/48 |
| 2006/0293702 A1 * | 12/2006 | Buser et al. | 606/185 |
| 2007/0018132 A1 * | 1/2007 | Gethmann et al. | 251/366 |
| 2007/0055274 A1 * | 3/2007 | Appenzeller et al. | 606/90 |
| 2007/0162072 A1 * | 7/2007 | Nicholas et al. | 606/205 |
| 2007/0225754 A1 * | 9/2007 | Measamer et al. | 606/205 |

FOREIGN PATENT DOCUMENTS

| | | |
|---|---|---|
| JP | 2005-73760 | 3/2005 |

OTHER PUBLICATIONS

U.S. Appl. No. 11/189,789 to Theroux et al., filed Jul. 27, 2005.
Japan Office action, mail date is May 10, 2011.

* cited by examiner

MEDICAL DEVICE WITH ADJUSTABLE INNER SHAFT MOVEMENT

FIELD OF THE INVENTION

This invention relates to a medical instrument including an electrosurgical apparatus, such as a laparoscopic instrument used for performing laparoscopic, pelvoscopic, arthroscopic, thoroscopic and/or similar such procedures, and more particularly to a medical device having a laparoscopic tube with an adjustable mechanism at a proximal end for controlling movement of an inner shaft within the laparoscopic tube.

BACKGROUND OF THE INVENTION

Medical procedures such as laparoscopy and the like, which employ a tip at the end of a tube for insertion into the patient, are beneficial because the incisions necessary to perform them are minimal in size, therefore promoting more rapid recovery and lower costs. For example, a patient who undergoes laparoscopic surgery may typically return to normal activity within a period of a few days to about a week, in contrast to more invasive procedures requiring a relatively larger incision (which may require about a month for recovery). (Although the term "laparoscopic" is typically used hereinafter, such use of the term "laparoscopic" should be understood to encompass any such similar or related procedures such as, for example, arthroscopic, endoscopic, pelvoscopic and/or thoroscopic or the like, in which relatively small incisions are used.)

Medical devices used in laparoscopic procedures typically include a handle or other actuation assembly, which is connected to a tube that extends from a proximal end near the actuation assembly to distal end of the tube, and the tube includes an inner shaft which also leads from the proximal end of the tube to the distal end of the tube. A tool-bearing tip is typically attached to the distal end of the tube and inner shaft, and the tool may be actuated—for example, if the tool includes shears, the blades of the shears may be opened and/or closed—by differential movement of the inner shaft relative to the tube.

In some laparoscopic medical devices, the tip (which typically includes a back hub for connection to the tube and a yoke for connection to the inner shaft) is attached to the tube and inner shaft by threading, and the correct operation of the tool depends on precise machining of two sets of threading—the first threading for connecting the tube to the tip, and the second threading for connecting the yoke of the tip to the inner shaft of the medical device (in which the first and second threadings may be of mutually different pitches, respectively; or, alternatively, of the same pitch). However, in some such implementations, the allowable assembled tolerance may be on the order of ±0.0015 inches for the distance between the tube end threading and the inner shaft threading when assembled with a pin, for example.

Such narrow tolerances often require intricate machining and manufacturing when making the medical devices and tips, and during production assemblers may often be required to repeatedly iterative processes—including multiple machining and testing steps—to make the fine adjustments necessary for the manufactured medical devices to function properly. This can lead to substantially increased production times and costs.

SUMMARY OF THE INVENTION

Accordingly, it is a feature of the present invention to provide an improved medical device which can adjust the movement of an inner shaft relative to a tube in the medical device.

In view of the above-noted, and other, features, the present invention provides a medical instrument in which the length along which an inner shaft within a tube can move lengthwise can be adjusted at a proximal end of the tube.

According to an aspect of the present invention, the medical device may include a tube having a first end and a second end, the first end for engaging an instrument tip; an inner shaft disposed in the tube, a shaft end connected to the inner shaft and which can move lengthwise relative to the tube; a first abutment surface to abut a first shaft end stop of the shaft end; and a second abutment surface to abut a second shaft end stop of the shaft end generally opposite the first shaft end stop of the shaft end, in which the shaft end can slidably move along a length constrained by the abutment of the first shaft end stop against the first abutment surface and the second shaft end stop against the second abutment surface, and in which either one or both of the first abutment surface or the second abutment surface is positionally adjustable relative to the tube.

The medical device may further have a lock nut including the first abutment surface and which can adjustably engage internal threading of the second end of the tube such that a position of the lock nut relative to the tube is adjustable. Also, the medical device may have a tube end housing to positionally adjustably engage the second end of the tube; a solid back stop including the first abutment surface and fixedly connected to the tube; and/or a forward stop including the second abutment surface, in which a position of the forward stop is adjustable relative to the tube.

In the medical device which has a lock nut, the lock nut may include a concavity to receive an adjustment tool. In addition, the first shaft end stop may be disposed outside the tube beyond the second end of the tube; and/or the medical device may further have a bearing block which includes the second abutment surface and which is fixed to an interior of the tube, in which the bearing block further includes a bearing to movably bear the shaft end. The medical device may also have a yoke disposed within the instrument tip and including shaft threads to threadingly engage the inner shaft, in which the tube includes threading at the first end of the tube to threadingly engage a back hub of the instrument tip, and in which a first pitch of the shaft threads is different from a second pitch of the first end threading; and may include a tool attached to the instrument tip, and an actuation assembly attached to the second end of the tube and which can move the inner shaft lengthwise relative to the tube when operated by a user, in which the tool of the instrument tip opens or closes by an extent corresponding to the position of the lock nut relative to the tube, and in which the abutment of the shaft end against the first and second abutment surfaces does not interfere with a travel limit of the instrument tip.

According to an alternative aspect of the present invention, a medical device may include a tube having a first end to engage an instrument tip and a second end having internal threading; an inner shaft extending within the tube substantially from the second end to the first end; a shaft end connected to the inner shaft and which can move lengthwise within the tube, the shaft end including a first surface aligned toward the first end of the tube and a second surface aligned toward the second end of the tube; a bearing stop fixedly disposed within the tube and which can abut the first surface of the shaft end; and a lock nut to abut the second surface of the shaft end and threadingly engaged with the internal threading of the tube such that the lock nut is positionally adjustable relative to the tube, in which the bearing stop includes a central recess along which the shaft end is movable. The shaft end may be able to slidably move along a length constrained by the abutment of the first surface of the shaft end against the bearing stop and the second surface of the shaft end against the lock nut.

Also, the medical device may further include a roller bearing fixed to the shaft end and which can roll against the bearing stop; the lock nut may include a bolt head; the medical device may further have a tool attached to the instrument tip and an actuation assembly attached to the second end of the tube and which can move the inner shaft lengthwise relative to the tube when operated by a user, in which the tool of the instrument tip opens or closes by an extent corresponding to the position of the lock nut relative to the tube, and in which the abutment of the shaft end against the lock nut and bearing stop does not interfere with a travel limit of the instrument tip.

The medical device may further include a handle having an elongated groove and a generally C-shaped cross-section and a bulbous protrusion fixedly connected to the shaft end and extending out from the second end of the tube, in which the bulbous protrusion is gripped within the elongated groove of the handle such that the bulbous protrusion can slide along the elongated groove when the handle is actuated.

According to further aspects of the present invention, a method for operating a medical device may include connecting a yoke of an instrument tip to a distal end of an inner shaft of a tube via first threading having a first pitch; connecting a back hub of the instrument tip to a distal end of the tube via second threading having a second pitch different from the first pitch of the first threading, the inner shaft generally coaxially disposed in the tube and operably engaged with a tool of the instrument tip; adjusting a position of either one or both of a first or second abutment surface relative to the tube; and limiting a range of travel of the inner shaft between the first and second abutment surfaces. The adjusting may include using an adjustment tool.

The method may further include actuating an actuation assembly of the medical device; moving the inner shaft relative to the tube in accordance with the actuating of the actuation assembly; and either opening and/or closing a tool of the instrument tip by an extent corresponding to the moving of the inner shaft. Also, the adjusting the lock nut may include rotating a bolt head fixedly attached to the lock nut and disposed generally outside the tube. In at least some forms of the method for operating the medical device, the limiting the range of travel of the inner shaft does not interfere with a travel limit of the instrument tip.

Other exemplary embodiments and advantages of the present invention may be ascertained by reviewing the present disclosure and the accompanying drawings.

BRIEF DESCRIPTION OF THE DRAWINGS

The present invention is further described in the detailed description which follows, in reference to the noted drawings by way of non-limiting examples of certain embodiments of the present invention, in which the numerals represent like elements throughout the several views of the drawings, in which.

DETAILED DESCRIPTION OF THE PREFERRED EMBODIMENTS

The particulars shown herein are by way of example and for purposes of illustrative discussion of the embodiments of the present invention only, and are presented for providing what is believed to be the most useful and readily understood description of the principles and conceptual aspects of the present invention. In this regard, no attempt is made to show structural details of the present invention in more detail than is necessary for the fundamental understanding of the present invention (although further exemplary details or structures may nonetheless be set forth herein, in order to illustrate examples of embodiments of the present invention), the description taken with the drawings making apparent to those skilled in the art how the several forms of the present invention may be embodied in practice.

Figure 1A:
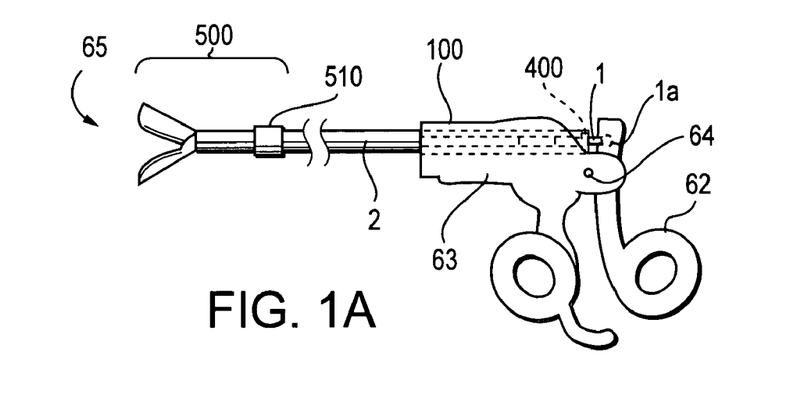
FIG. 1A is a schematic side elevational view illustrating an example of a laparoscopic medical device including a tip engaged with a tube.
Figure 1B:
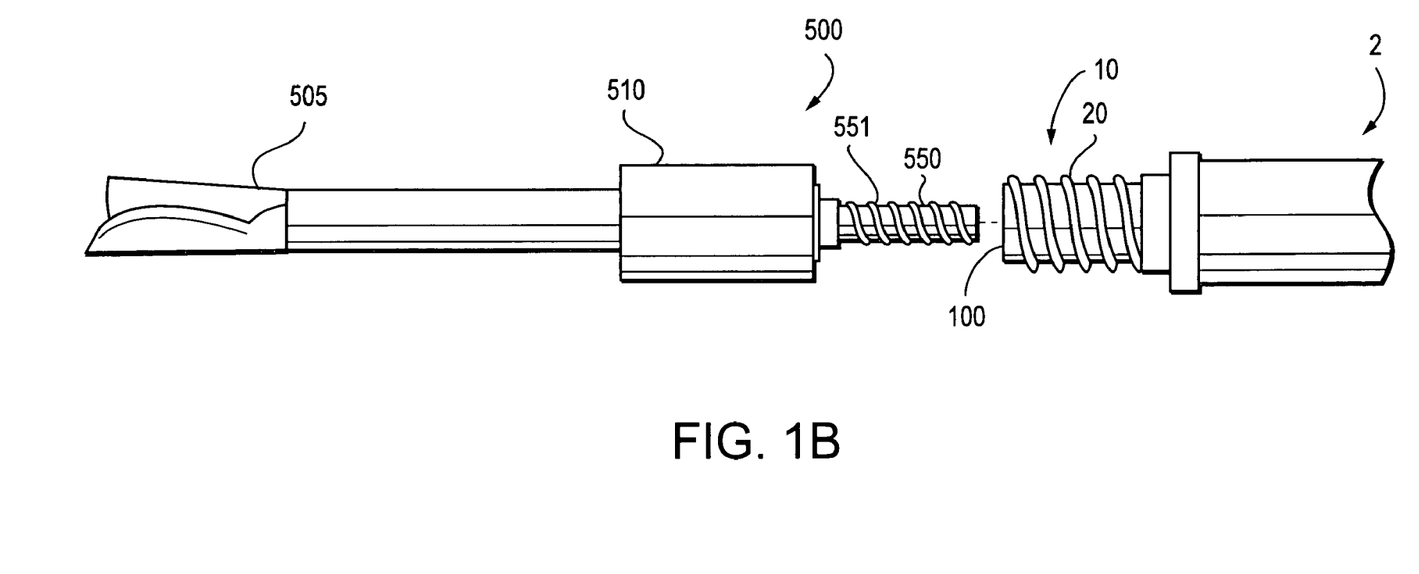
FIG. 1B is a side elevational view illustrating a tip detached from a distal end of the laparoscopic medical device shown in FIG. 1A.

Referring to FIGS. 1A and 1B, a medical device 65 for performing laparoscopic surgery or the like, such as excision of tissue (either with or without cauterization), for example, may typically include (but is not limited to) a tip 500 having a tool 505 such as shears, pincers or a grasping tool, for example, in which the tip 500 may engage with a distal tube end 10 (in other words, the end of the tube 2 farthest from the operator of the medical device 65) of a tube 2 which extends from a base portion 63 connected to handles 62 (or other suitable control device or actuation assembly) operable by the medical personnel or physician performing a surgical or medical procedure. As shown in FIG. 1B, for example, a laparoscopic tube end 10 according to a first embodiment of the present invention may include first threading 20 (which may threadingly engage and/or attach to a back hub 510 of the tip 500).

A proximal end of the tube 2 (in other words, the end of the tube 2 closest to the operator of the medical device 65) may extend through to a rear of the base portion 63 and protrude therefrom, with a ball 1a or other bulbous protrusion of a shaft end 1 sticking out from the proximal end of the protruding tube 2. The handles 62 may reciprocally pivot about a hinge 64, when the operator actuates the handles 62 to open and/or close the device 65. Although the end portion of the shaft end 1 is exemplified in the form of a ball 1a or other bulbous protrusion, it is readily understood by those skilled in the art that in accordance with the present invention, this feature may alternatively take any other suitable form including, but not limited to, a disk, a peg, a square or rounded square block, a lever, etc., for example.

Further, the yoke 550 may engage with an inner shaft 100 using, for example, second threading 551. The first threading 20 and second threading 551 may have respectively different pitches, or alternatively, they may have identical pitch.

The tool 505 opens and/or closes (or is otherwise operated) by the relative movement of the inner shaft 100 with respect to the tube 2; however, in order for the yoke 550 to appropriately engage the inner shaft 100 while the back hub 510 correctly engages the first threading 20, it is necessary for the inner shaft 100 to be correctly positioned initially with regard to the tube 2. Manipulation of the inner shaft 100 at the laparoscopic tube end 10 may be difficult, impossible and/or impractical—accordingly, the present invention permits substantially infinitely fine adjustment at the proximal end of the tube 2.

Figure 2:
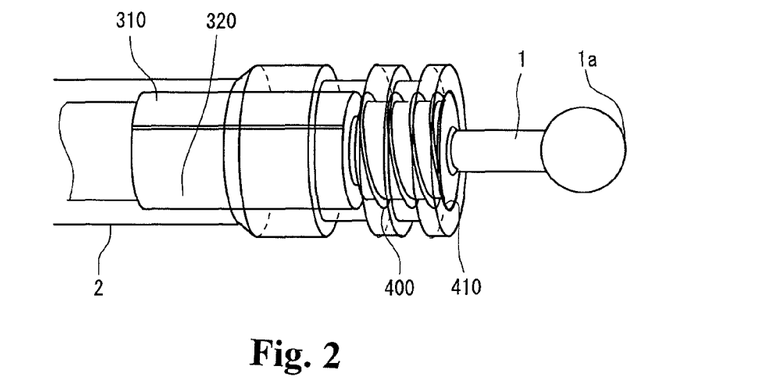
FIG. 2 is an oblique partial cutaway view illustrating a proximal end of the tube, an inner shaft, a shaft end and a lock nut in accordance with a first embodiment of the present invention.
Figure 3:
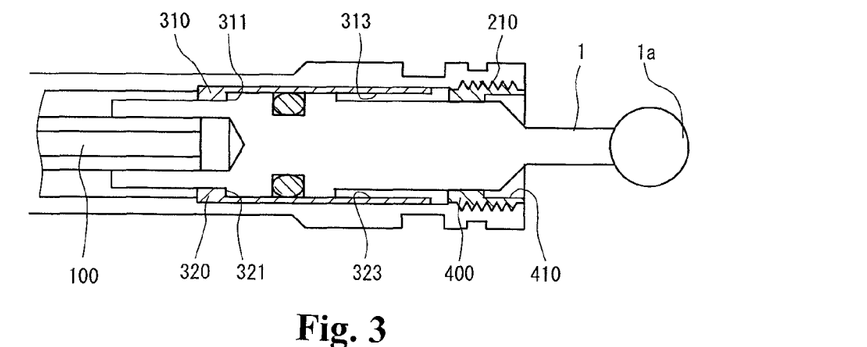
FIG. 3 is a side cutaway view illustrating a proximal end of the tube and the components associated with the proximal end of the tube when the inner shaft and shaft end are in an "open" instrument position, according to the first embodiment.
Figure 4:
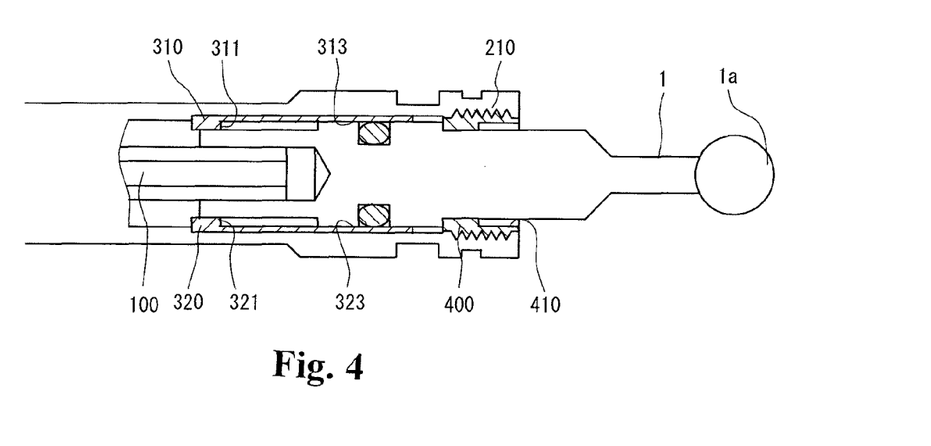
FIG. 4 is a side cutaway view illustrating a proximal end of the tube and the components associated with the proximal end of the tube when the inner shaft and shaft end are in a "closed" instrument position, according to the first embodiment.

As shown in FIGS. 2-4, for example, the inner shaft 100 within the tube 2 is connected to a shaft end 1 (at the end of which may be attached a ball 1a). Within the tube 2, first and second bearing stops 310 and 320 may surround the shaft end 1, and the shaft end 1 may move lengthwise within the tube 2 by virtue of a bearing or bearings (which may be a roller bearing, fluid bearing, or any other suitable bearing) by rolling along the bearing stops 310 and 320. Alternatively, for example, the shaft end 1 may move lengthwise within the tube 2 by an oil or fluid bearing, by frictional sliding, or by any other suitable configuration.

Extending inward from the extreme edge of the tube 2 may be internal threading 210. Furthermore, the proximal end of the tube 2 may have a lock nut 400 threadingly engaged with the internal threading 210 within the tube 2 (although any other suitable adjustable engagement technology may otherwise be used for adjustably engaging the tube 2 and the lock nut 400, such as, for example, a frictional press fit, a peg-and-socket mechanism, a barrel pin and matching concavity, etc.). The lock nut 400 may include a concavity 410 into which a tool or finger may be inserted to adjust the position of the lock nut 400 relative to the tube 2 by twisting the lock nut 400 within the internal threading 210. For example, a user may adjust the lock nut 400 farther into the tube 2 by turning the lock nut 400 clockwise (e.g., to shorten the displacement of the inner shaft 100); and conversely, the user may adjust the lock nut 400 out from the tube 2 by twisting the lock nut 400 in a counter-clockwise direction (e.g., to lengthen the displacement of the inner shaft 100). For example, the concavity 410 may have a generally circular shape extending around the outer circumference of the shaft end 1 (as exemplified in FIGS. 3 and 4, for example); however, alternatively, the concavity 410 might have an angular shape (e.g., hexagonal or rectangular, inter alia) such as is commonly used in an Allen wrench or key-and-socket type tool, or any other suitable shape, and may not be open around the entire outer circumference of the shaft end 1, etc.

The bearing stops 310 and 320 may be fixed within the tube 2 by any appropriate method, such as, for example, adhesives, threading, welding and/or casting to be formed as a single body with the proximal end of the tube 2. Also, a seal or gasket 110 (which may be made of an elastic material such as an elastomeric polymer, plastic, polyethylene, polyether ether ketone, rubber, gel or any other suitable material, for example) may also be disposed between the shaft end and the interior surface of the tube 2, for example (although alternatively, the seal or gasket 110 may be omitted). The seal or gasket 110 may seal the interior of the tube 2 from the outside environment, for example, and may have the form of an O-ring or any other suitable shape. The bearing stops 310 and 320 further include a respective central recess 313, 323 along which the shaft end 1 is movable.

The "play" or length along which the shaft end 1 (and correspondingly the inner shaft 100) may travel is constrained by the abutment surfaces 311 and 321 of the first and second bearing stops 310 and 320, respectively, as a distalmost point to which the shaft end 1 may travel toward the distal end of the tube 2, on the one hand; and is constrained in the opposite direction by the lock nut 400 as a proximalmost extent to which the shaft end 1 (and therefore the inner shaft 100) may travel toward the proximal end of the tube 2. As shown in FIG. 3, for example, a flange or flare at the distal portion of the shaft end 1 abuts against and is stopped by the abutment surface 311 of the first bearing stop 310 and the abutment surface 321 of the second bearing stop 320 when urged in the distalward direction, and is stopped from traveling past the lock nut 400 in the proximalward direction by either the same or another flange or flare disposed on the proximal portion of the shaft end 1 when that flange or flare abuts against and is stopped by a corresponding flange or flare of the lock nut 400.

FIG. 4 illustrates the latter example, and shows the flare of the shaft end 1 abutting the lock nut 400. As such, the surgeon, assembler or other user of the medical device 65 can open and/or close the tool 505 at the distal end of the tube 2, by actuating the handle 62 (which may have an elongated groove [not shown] extending along a top portion thereof, and which may have a cross-section generally similar to a letter 'C' so that the elongated groove can grip the ball 1a or bulbous protrusion, as illustrated in FIG. 1A, for example) to pull and/or pushing the ball 1a (or bulbous protrusion) of the shaft end 1, and thus slide the shaft end 1 and inner shaft 100 lengthwise within the tube 2 between the proximalmost and distalmost points established by the lock nut 400 on the one hand, and the first and second bearing stops 310 and 320 on the other hand.

As an advantage, because adjustment of the freedom of movement of the inner shaft 100 relative to the tube 2 can be made at the proximal end of the tube 2, the requirements of fine machining or other intricate assembly processes for threading at the distal end of the tube 2 may be reduced or eliminated; and furthermore, the ease of use of the medical device 65 may be enhanced.

Figure 5:
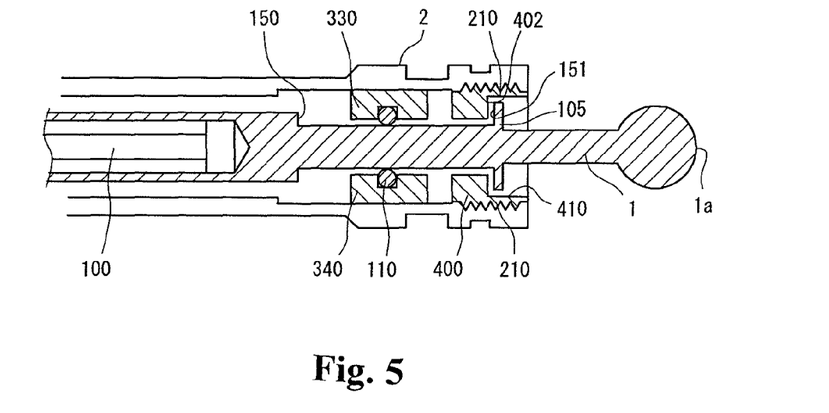
FIG. 5 is a cutaway view illustrating a proximal end of a tube of a medical device according to a second embodiment of the present invention.

A second embodiment of the present invention is exemplified in FIG. 5, which shows a proximal end of a tube 2 generally similar to the first embodiment; except that rather then having a flare or flange extend convexly from the center portion of the shaft end 1, the shaft end 1 instead has a central portion which is reduced in radius and into which a first bearing block 330 and second bearing block 340 may generally protrude. In addition, the bearing may be fixed to the bearing blocks 330 and/or 340, instead of being fixed to the shaft end 1 (as exemplified in the first embodiment); also, the gasket or seal 110 may likewise alternatively be fixed to the bearing blocks 330 and/or 340 rather than to the shaft end 1, for example.

Furthermore, as shown in FIG. 5, the shaft end 1 includes a shaft end stop 150 within the tube 2 which abuts and is stopped by the first and second bearing blocks 330 and 340 when the shaft end 1 is pulled to a proximalmost position. Conversely, a flare 105 (which may alternative be described as a flange or surface) of the shaft end 1 is positioned generally outside the tube 2 (in a proximalward direction) and includes a shaft end stop 150 for abutting the lock nut 400 on a proximal-facing surface (herein referred to as the "shaft end stop 150") of the lock nut 400 within the concavity 410 of the lock nut 400. Thus, when the shaft end 1 is pushed into the tube 2 to a distalmost position relative to the tube 2, the flare 105 abuts the shaft end stop 150 of the lock nut 400, and therefore stops the travel of the shaft end 1 and inner shaft 100 in the distalward direction.

Figure 6:
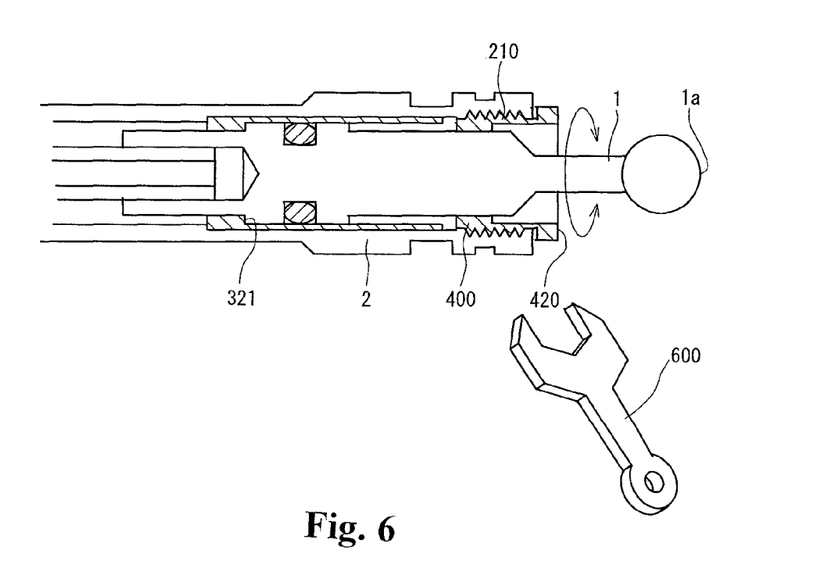
FIG. 6 is an oblique partial cutaway view illustrating a proximal end of a tube and a shaft end having a bolt head, according to a third embodiment of the present invention.

FIG. 6 shows a third embodiment of the present invention, which in many aspects may be generally similar to the first and/or second embodiments (or any other suitable embodiment of the present invention), and further includes a bolt head 420 fixed to the lock nut 400. The bolt head 420 may be formed separately from the lock nut 400 and then later welded or otherwise attached to lock nut; or, alternatively, the bolt head 420 may be substantially integrally formed of a single material with the lock nut 400 by casting or machining (or any other suitable method), for example. Using the bolt head 420, which may include a hex pattern which fits into a standard or non-standard wrench 500, the bolt head 420 and therefore the lock nut 400 may be adjusted either by hand or with a tool such as the wrench 500.

As an advantage, by having the bolt head 420 which extends out beyond the tube 2, a non-standard tool (which may be delicate or difficult to procure or manipulate) is not required to be inserted into a concavity 410 in between the shaft end 1 and the lock nut 400; rather, a standard tool such as a wrench 500 may instead be used to twist and/or adjust the lengthwise position of the lock nut 400 relative to the tube 2 in the threading 210.

Figure 7:
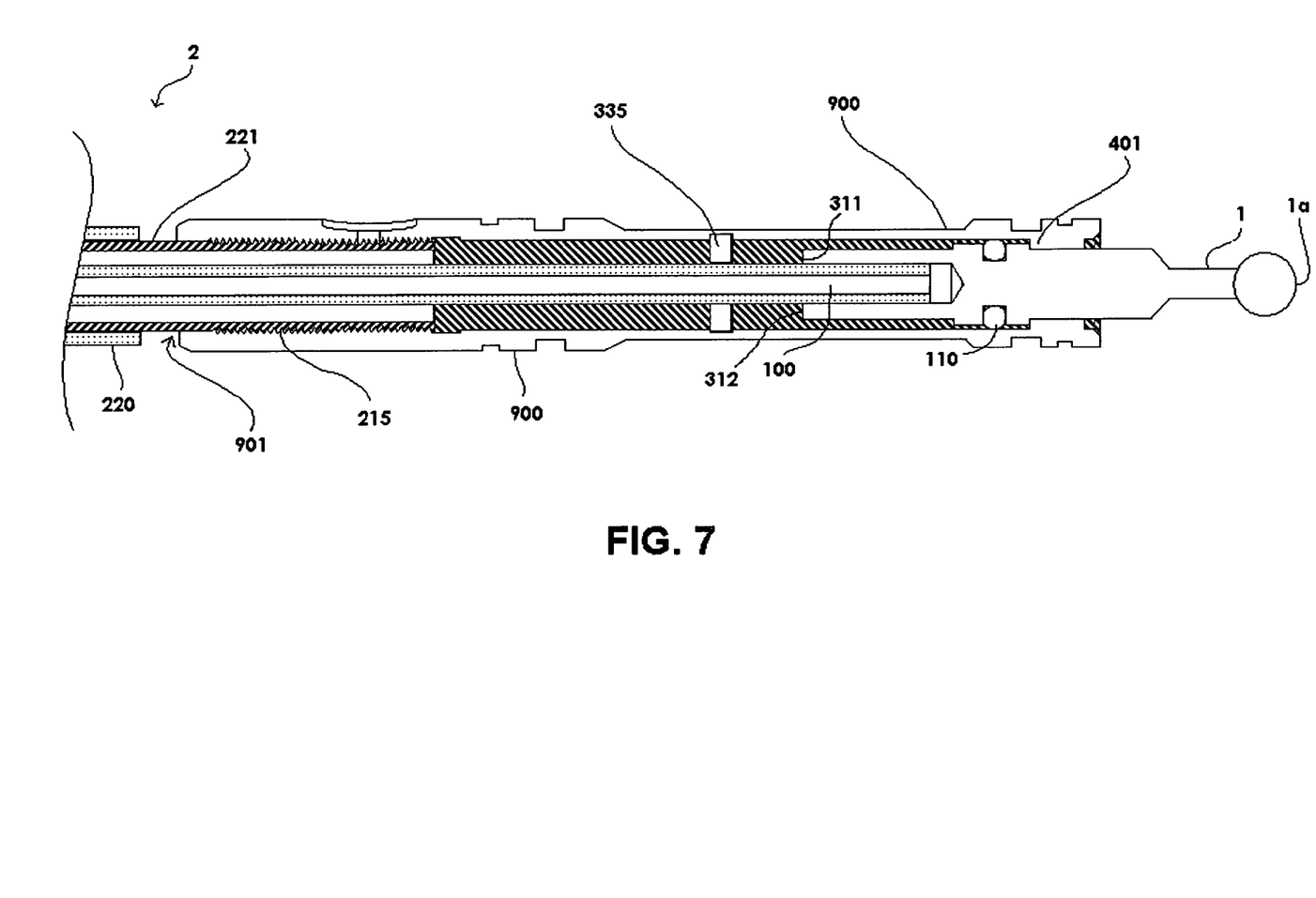
FIG. 7 is a side cutaway view illustrating a proximal end of the tube and a tube end housing having an adjustable forward stop, according to a fourth embodiment of the present invention.

FIG. 7 shows a proximal end of a tube 2 according to a fourth embodiment of the present invention, which in various aspects may be generally similar to any of the above-described embodiments (or any other suitable embodiment of the present invention), and which includes one or more forward stops 335 which are disposed within the interior of a tube end housing 900 adjustably attached to the proximal end of the tube 2, and one or more solid back stops 401. The forward stops 335 may be fixedly or adjustably positioned in the tube end housing 900 by, for example, welding, press fit, threading, use of a snap ring, or any other suitable positioning technology. By adjusting the position of the tube end housing 900 relative to the tube 2, the forwardmost and distalmost positions to which the shaft end 1 can travel relative to the tube 2 can also be adjusted, without necessarily requiring (although conversely, not prohibiting the use of) an adjustment tool (as a user may simply adjust the relative position by twisting the entire tube end housing 900 by hand, for example).

The tube end housing 900 may include one or more solid back stops 401 for halting movement of the shaft end 1 in the proximalward direction, and the solid back stops 401 may be formed integrally with the tube end housing 900, for example. As an alternative, the solid back stops 401 may be formed separately from the tube end housing 900 and affixed thereto by, for example, welding, adhesive, frictional fitting or press fit, threading, or any other suitable method, for example.

As shown in FIG. 7, for example, the laparoscopic device may include a sheath 220 extending from generally near or at the tube end housing 900 to generally near or at the distal end of the tube 2, and the inner shaft 100 may be enclosed by a sleeve 221 that may be adjustably engaged with the tube 2 (by threading 215, for example). As an alternative to the threading 215, the sleeve 221 may be fixed to the tube 2 by frictional or press fitting, a snap ring, a barrel pin and hole, a ratchet-type mechanism, or any other suitable method. Further, the bearing along which the inner shaft 100 moves may be generally coextensive with the sleeve 221 and/or disposed on the forward stops 335, for example (e.g., as a roller bearing, fluid bearing and/or telescoping bearing, inter alia). As a result, the necessity of a bearing near the proximal end of the tube 2 may be obviated, for example.

As an example of how a laparoscopic device according to the seventh embodiment may operate, a user (such as, for example, a surgeon, assistant, tool assembler or the like) may attach and/or engage the tube end housing 900 to the tube 2 by inserting the exposed threaded portion 215 of the sleeve 221 of the tube 2, which extends beyond the sheath 220, into an orifice 901 of the tube end housing 900. The user may then threadingly engage the tube end housing 900 with the tube 2 via the threading 215 by twisting the tube 2 and/or tube end housing 900. Also, the user may adjust the freedom of travel of the shaft end 1 by threadingly adjusting the position of the tube end housing 900 relative to the tube 2, in order to set or adjust the position of the solid back stop 401 and/or the forward stop 335.

As a further alternative, the solid back stop 401 may include a lock nut 400 adjustably disposed in the tube end housing 900 as set forth in any of the above-described embodiments, for example, and/or the forward stop 335 may also be adjustably disposed (by threading, snap ring, press fit or any other suitable method) within the tube end housing 900. In such a configuration, the convenience of the laparoscopic device 65 may be enhanced because both the distalward and proximalward movement of the shaft end 1 can be adjusted, for example. According to yet another alternative, the sleeve 221 may have the threading 215 on an interior surface of the sleeve 221, and the tube end housing 900 may be externally threaded—in such an implementation, the threaded part of the tube end housing 900 may be fitted into the sleeve 221, for example.

In addition, although the laparoscopic device 65 has been exemplified as including a tool 505 in the form of shears on a tip 500, it is to be understood that the present invention is not limited thereto but may alternatively include, for example, a grasping tool, an optical device and/or light, an electrical or heat cauterization tool, or any other tool suitable for use in a laparoscopic or other surgical or medical device. Furthermore, tip travel limits on the tip 500 may generally not necessarily be interfered with by the adjustable constraints on the proximalward and/or distalward movement of the shaft, in accordance with certain embodiments of the present invention.

It is noted that the foregoing examples have been provided merely for the purpose of explanation and are in no way to be construed as limiting of the present invention. While the present invention has been described with reference to certain embodiments, it is understood that the words which have been used herein are words of description and illustration, rather then words of limitation. Changes may be made, within the purview of the appended claims, as presently stated and as amended, without departing from the scope and spirit of the present invention in its aspects.

Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:
1. A medical device, comprising:
   a tube having a first end and a second end, the first end configured to engage an instrument tip;
   an inner shaft disposed in the tube;
   a shaft end connected to the inner shaft and configured to move lengthwise relative to the tube;

a first abutment surface within the tube and configured to disengagingly abut a first shaft end stop of the shaft end upon lengthwise movement of the shaft end in a first direction; and a second abutment surface within the tube and configured to disengagingly abut a second shaft end stop of the shaft end generally opposite the first shaft end stop of the shaft end upon lengthwise movement of the shaft end in a direction opposite the first direction, wherein the shaft end is configured to slidably move along a length constrained by the abutment of the first shaft end stop against the first abutment surface and the second shaft end stop against the second abutment surface, and wherein at least one of the first abutment surface or the second abutment surface is positionally adjustable relative to the tube such that a range of longitudinal travel of the inner shaft is adjustable, wherein the device further comprises a yoke disposed within the instrument tip and including shaft threads configured to threadingly engage the inner shaft, wherein the tube includes threading at the first end of the tube configured to threadingly engage a back hub of the instrument tip, and wherein a first pitch of the shaft threads is different from a second pitch of the first end threading.

2. The medical device according to claim 1, further comprising a lock nut including the first abutment surface and configured to adjustably engage internal threading of the second end of the tube such that a position of the lock nut relative to the tube is adjustable.

3. The medical device according to claim 1, further comprising:
a tube end housing configured to positionally adjustably engage the second end of the tube; and
a solid back stop including the first abutment surface and fixedly connected to the tube.

4. The medical device according to claim 1, further comprising a forward stop including the second abutment surface, wherein a position of the forward stop is adjustable relative to the tube.

5. The medical device according to claim 2, wherein the lock nut includes a concavity configured to receive an adjustment tool.

6. The medical device according to claim 1, wherein the first shaft end stop is disposed outside the tube beyond the second end of the tube.

7. The medical device according to claim 1, further comprising a bearing block which includes the second abutment surface and which is fixed to an interior of the tube,
wherein the bearing block further includes a bearing configured to movably bear the shaft end.

8. The medical device according to claim 1, further comprising:
a tool attached to the instrument tip; and
an actuation assembly attached to the second end of the tube and configured to move the inner shaft lengthwise relative to the tube when operated by a user,
wherein the tool of the instrument tip opens or closes by an extent corresponding to the position of the lock nut relative to the tube, and
wherein the abutment of the shaft end against the first and second abutment surfaces does not interfere with a travel limit of the instrument tip.

9. A medical device, comprising:
a tube having a first end configured to engage an instrument tip and a second end having internal threading;
an inner shaft extending within the tube substantially from the second end to the first end;
a shaft end connected to the inner shaft and configured to move lengthwise within the tube, the shaft end including a first surface aligned toward the first end of the tube and a second surface aligned toward the second end of the tube;
a bearing stop fixedly disposed within the tube and configured to disengagingly abut the first surface of the shaft end; and
a lock nut configured to abut the second surface of the shaft end and threadingly engaged with the internal threading of the tube such that the lock nut is positionally adjustable relative to the tube and such that a range of longitudinal travel of the inner shaft is adjustable,
wherein the bearing stop includes a central recess along which the shaft end is movable,
wherein the device further comprises a yoke disposed within the instrument tip and including shaft threads configured to threadingly engage the inner shaft,
wherein the tube includes threading at the first end of the tube configured to threadingly engage a back hub of the instrument tip, and
wherein a first pitch of the shaft threads is different from a second pitch of the first end threading.

10. The medical device according to claim 9, wherein the shaft end is configured to slidably move along a length constrained by the abutment of the first surface of the shaft end against the bearing stop and the second surface of the shaft end against the lock nut.

11. The medical device according to claim 9, further comprising a roller bearing fixed to the shaft end and configured to roll against the bearing stop.

12. The medical device according to claim 9, wherein the lock nut includes a bolt head.

13. The medical device according to claim 9, further comprising:
a tool attached to the instrument tip; and
an actuation assembly attached to the second end of the tube and configured to move the inner shaft lengthwise relative to the tube when operated by a user,
wherein the tool of the instrument tip opens or closes by an extent corresponding to the position of the lock nut relative to the tube, and
wherein the abutment of the shaft end against the lock nut and bearing stop does not interfere with a travel limit of the instrument tip.

14. The medical device according to claim 9, further comprising:
a handle having an elongated groove and a generally C-shaped cross-section; and
a bulbous protrusion fixedly connected to the shaft end and extending out from the second end of the tube,
wherein the bulbous protrusion is gripped within the elongated groove of the handle such that the bulbous protrusion can slide along the elongated groove when the handle is actuated.

15. A method for operating a medical device, the method comprising:
connecting a yoke of an instrument tip to a distal end of an inner shaft of a tube via first threading having a first pitch;
connecting a back hub of the instrument tip to a distal end of the tube via second threading having a second pitch different from the first pitch of the first threading, the inner shaft generally slidably coaxially disposed in the tube and operably engaged with a tool of the instrument tip;

adjusting a position of at least one of a first or second abutment surface relative to the tube; and limiting, via the adjusted at least one of the first and second abutment surfaces, a range of travel of the inner shaft between the first and second abutment surfaces.

16. The method according to claim 15, wherein the adjusting includes using an adjustment tool.

17. The method according to claim 15, further comprising:
actuating an actuation assembly of the medical device;
moving the inner shaft relative to the tube in accordance with the actuating of the actuation assembly; and
one of opening or closing a tool of the instrument tip by an extent corresponding to the moving of the inner shaft.

18. The method according to claim 15, wherein the adjusting includes rotating a bolt head fixedly attached to the lock nut and disposed generally outside the tube.

19. The medical device according to claim 15, wherein the limiting the range of travel of the inner shaft does not interfere with a travel limit of the instrument tip.

20. The medical device according to claim 9, wherein:
the bearing stop is configured to disengagingly abut the first surface of the shaft end upon lengthwise movement of the shaft end in a first direction; and
the lock nut is configured to abut the second surface of the shaft end upon lengthwise movement of the shaft end in a direction opposite the first direction.

* * * * *